United States Patent [19]
Anderson

[11] Patent Number: 4,954,562
[45] Date of Patent: Sep. 4, 1990

[54] WATER ABSORBENT RESINS
[75] Inventor: Mark Anderson, Wheaton, Ill.
[73] Assignee: American Colloid Company, Arlington Heights, Ill.
[21] Appl. No.: 303,815
[22] Filed: Jan. 30, 1989

Related U.S. Application Data

[63] Continuation-in-part of Ser. No. 854,000, Apr. 21, 1986, Pat. No. 4,677,174, Ser. No. 872,654, Jun. 10, 1986, Pat. No. 4,755,562, and Ser. No. 67,233, Jun. 25, 1980, Pat. No. 4,802,773.

[51] Int. Cl.$^5$ .................... C08K 3/22; C08F 8/32
[52] U.S. Cl. ........................... 524/779; 524/780; 524/783; 524/784; 524/785; 524/786; 524/789; 524/430; 526/240; 526/95; 525/381; 525/382
[58] Field of Search .................. 526/95, 240, 430; 524/430, 779, 780, 783, 784, 785, 786, 787; 525/381, 382

[56] References Cited

U.S. PATENT DOCUMENTS 4,183,991  1/1980  Smiley et al. .............. 524/430
4,286,082  8/1981  Tsubakimoto et al. ........ 526/240
4,552,938  11/1985 Mikita et al. .............. 526/240
4,612,250  9/1986  Takedo et al. .............. 428/500
4,794,140  12/1988 Alexander ................. 524/827

Primary Examiner—Peter F. Kulkosky
Attorney, Agent, or Firm—Marshall, O'Toole, Gerstein, Murray & Bicknell

[57] ABSTRACT

Improved water-absorbing, crosslinked acrylate resins are prepared by aqueous polymerization of (A) acrylic acid neutralized 70 to 100 mole percent for example with ammonia and/or caustic alkali and/or an amine; with (B) acrylamide in a mole ratio of 70 to 100 mole percent (A) to 30:0 mole percent (B); (C) styrene, in an amount of 0% to 25% based on the weight of acrylic acid or acrylate; and (D) a water miscible or a water soluble polyvinyl monomer in the presence of (E) a metal oxide, such as titanium dioxide, in an amount of 0.001% to 5% based on the total weight of (A), (B), (C), (D) and (E), such that the amount of (D) is 0.001 to 0.6 weight percent based on the total weight of (A), (B), (C), (D) and (E). In addition, surface treating the water-absorbing crosslinked acrylate resins with a polyquaternary amine substantially further increases both the rate of water absorption and the quantity of water absorbed and retained by the metal oxide-containing resin. The untreated and the surface-treated resins also maintain the necessary "dry feel" required for most applications.

44 Claims, No Drawings

WATER ABSORBENT RESINS

CROSS-REFERENCE TO RELATED APPLICATION

This application is a continuation-in-part of my co-pending applications, Ser. No. 854,000, filed on Apr. 21, 1986 now U.S. Pat. No. 4,677,174, issued on June 30, 1987, Ser. No. 872,654, filed on June 10, 1986 now U.S. Pat. No. 4,755,562 issued on July 5, 1988 and Ser. No. 067,233 filed on June 25, 1987 now U.S. Pat. No. 4,802,773.

FIELD OF THE INVENTION

The present invention relates to a method of manufacturing water-absorbent resins having improved water-absorbing and water-retaining properties and more particularly to a process of preparing crosslinked homopolymers and copolymers of acrylic acid in the presence of a metal oxide, such as titanium dioxide. In addition, the present invention relates to a method of surface treating a water-absorbent resin, such as a neutralized, crosslinked, homopolymer or copolymer of acrylic acid including a metal oxide, with a polyquaternary amine to improve the water absorption and water retention properties of the resin.

BACKGROUND OF THE INVENTION

Water-absorbing resins have found wide use in sanitary goods, hygienic goods, wiping cloths, water retaining agents, dehydrating agents, sludge coagulants, disposable towels and bath mats, disposable door mats, thickening agents, disposable litter mats for pets, condensation preventing agents and release control agents for various chemicals. Water-absorbing resins are available in a variety of chemical forms including substituted and unsubstituted natural and synthetic polymers such as hydrolysis products of starch-acrylonitrile graft polymers, carboxymethylcellulose, crosslinked polyacrylates, sulfonated polystyrenes, hydrolyzed polyacrylamides, polyvinyl alcohols, polyethylene oxides, polyvinylpyrrolidines and polyacrylonitriles.

Each type of water-absorbing resin differs in ease and cost of manufacture, chemical and physical properties, rate of water-absorption, and degree of water-absorption and retention. For example, the hydrolysis products of starch-acrylonitrile graft polymers have a comparatively high ability to absorb water, but require a cumbersome process for production and have the disadvantages of low heat resistance and decaying or decomposing easily due to the presence of starch. Conversely, other water-absorbent polymers are easily and cheaply manufactured and are not subject to decomposition, but do not absorb liquids as well as the starch-acrylonitrile graft polymers.

Therefore, it would be extremely advantageous to provide a method of increasing the water absorption properties of a stable, easy to manufacture waterabsorbing resin to match the superior water-absorption properties of a difficult to manufacture polymer. Likewise, it would be advantageous to increase the liquid absorption properties of an already superior water-absorbent resin.

One of the processes for polymerizing acrylic acid and acrylates is aqueous solution polymerization. The polymer obtained by this process is soluble in water and, therefore, is crosslinked to modify the polymer into a useful water-absorbing resin. However, even if the modification is effected by reacting a crosslinking agent concurrently with or after aqueous solution polymerization, the resulting reaction product is in the form of a difficult to handle, highly viscous aqueous solution, or a gel, containing absorbed water. As a result, the aqueous solution or gel must be dehydrated (dried) to obtain a water-absorbing resin in the desired solid or powder form. However, it is difficult to dry the reaction product efficiently by the usual rotary drum roller method or spray drying method because care must be taken to avoid the excessive crosslinking that results from overheating during drying. Furthermore, insufficient drying of the resin results in reduced crosslinking density. Therefore, extreme difficulties are encountered in preparing a resin having a desired low water content and good water-absorbing ability.

Any method of improving the water-absorbing properties of a resin must also retain the "dry feel" of the resin after liquid absorption. Although water and liquid absorption is the primary function of the water-absorbing resin, in many applications, such as in disposable diapers, catamenial devices and surgical dressings, it is almost equally important that the polymer maintain its "dry feel". The polymer must be able to absorb amounts of water several times its weight, plus be sufficiently crosslinked to avoid partial solubilization of the polymer to form a gel and lead to a slippery, wet feeling. Presently, water-absorbing resins, such as crosslinked polyacrylic acid, do possess a "dry feel" after significant water absorption. Thus any methods directed to improving the water-absorbing properties of such a resin should not alter the basic "dry feel" of the resin after liquid absorption.

Any method that both increases the water-absorbing capabilities of a water-absorbent resin and maintains the basic "dry feel" of the resin would enhance and broaden the application possibilities of many water-absorbent polymers. Such a method should be simple and economical to avoid increases in the raw material or the manufacturing cost of the waterabsorbent resin.

SUMMARY OF THE INVENTION

In brief, the present invention is directed to a process for preparing improved water-absorbent crosslinked resins, of low water content, by aqueous solution polymerization without any additional dehydrating or drying step. The present invention also is directed to a method of surface treating a waterabsorbent resin with a sufficient amount of polyquaternary amine to substantially improve the water-absorbent and water retention properties of the resin. It has been found that the surface treatment can be applied to a dried polymer at any time, either immediately prior to using the polymer or by incorporating the treatment into a manufacturing step immediately following the polymerization reaction and polymer drying steps.

Another object of the present invention is to provide a process for preparing a crosslinked resin by the aqueous polymerization of partially or fully neutralized acrylic acid and a water-miscible to water soluble polyvinyl monomer in the presence of a metal oxide, such as titanium dioxide, in a combined concentration of 30 to 80% by weight partially or fully neutralized acrylic acid and 0.001% to 5% metal oxide, based on the total weight of the aqueous polymerizable solution.

Another object of the present invention is to provide a process for preparing a crosslinked resin by polymerization of acrylic acid neutralized 70–100 mole percent and a polyvinyl monomer, in the presence of a metal oxide, in proportions of 30 to 80% by weight partially or fully neutralized acrylic acid; 0.001 to 5% of a metal oxide, based on the total weight of the polymerizable solution; 0% to 25% by weight styrene, based on the weight of acrylic acid; and 0% to 30% by weight acrylamide, based on the weight of acrylic acid, in aqueous solution.

Another object of the present invention is to provide a process for producing a water-absorbent resin crosslinked with 0.2 weight percent to 0.6 weight percent based on the total weight of monomers and metal oxide, of a water miscible or water soluble polyvinyl monomer crosslinking agent to achieve a "dry feel" to the resin after significant water absorption.

Another object of the present invention is to provide a water-absorbent resin having improved water-absorption and water-retention properties by polymerizing the partially or completely neutralized acrylic acid in the presence of a metal oxide.

Another object of the present invention to surface treat water-absorbent resins to substantially increase the water absorption and water retention properties of the polymer.

Another object of the present invention is to surface treat water-absorbent resins with a polyquaternary amine to substantially increase the water absorption and water retention properties of the resins.

Another object of the present invention is to provide a process for producing a polyacrylate resin copolymer, in the presence of a metal oxide and crosslinked with 0.2 weight percent to 0.6 weight percent based on the total weight of monomers and metal oxide of a water miscible or water soluble polyvinyl monomer crosslinking agent, and thereafter contacting the resin with a polyquaternary amine in an amount sufficient for interaction to substantially improve the water absorbency and water retention properties of the resin and to maintain a "dry feel" to the resin after significant water absorption.

In brief, the present invention is directed to a process for preparing water-absorbing, crosslinked resins by aqueous polymerization of (A) acrylic acid neutralized 70 to 100 mole percent for example with ammonia and/or caustic alkali and/or an amine; with (B) acrylamide in a mole ratio of 70 to 100 mole percent (A) to 30:0 mole percent (B); (C) styrene, in an amount of 0% to 25% based on the weight of acrylic acid or acrylate; and (D) a water miscible or a water soluble polyvinyl monomer; in the presence of (E) a metal oxide, in an amount of .001% to 5% based on the total weight of (A), (B), (C), (D) and (E), such that the amount of (D) is 0.001 to 0.6 weight percent based on the total weight of (A), (B), (C), (D) and (E). To achieve the full advantage of the present invention the concentration of monomers (A), (B), (C), (D) and of metal oxide (E) is at least 50 wt. % of the aqueous solution. During synthesis, the resin dries to an acceptable water content of at least less than 15% by weight of the polymer, and thereafter the resin is contacted with a polyquaternary amine in an amount sufficient for interaction to substantially improve the water-absorbent and water-retention properties of the resin. A "dry feel" is obtained at a polyvinyl monomer concentration of at least 0.2 wt. percent of the aqueous solution.

In accordance with an important embodiment of the present invention, a heated aqueous solution comprising (A) acrylic acid neutralized 70 to 100 mole percent for example with ammonia, and/or caustic alkali and/or an amine; (B) styrene, in an amount of 0% to 25% based on the weight of acrylic acid or acrylate; and (C) a metal oxide, like titanium dioxide, in an amount of 0.001% to 5% based on the total amount of (A), (B), (C) and (D); and (D) a water-miscible to water-soluble polyvinyl monomer; water and, when desired, an organic solvent having a boiling point of 40 to 150° C., and having a metal oxide-monomer concentration of (A) plus (B) plus (C) plus (D) of 30 to 80 wt. % is subjected to polymerization in the presence of one or more polymerization initiators without external heating while allowing water to evaporate. After sufficient water has evaporated such that the resin includes about 15% by weight water or less, the resin is contacted with a polyquaternary amine to substantially further increase the water absorbency and water retention properties of the polymer.

The above and other objects and advantages of the present invention will become apparent from the following detailed description of the present invention.

DETAILED DESCRIPTION OF THE INVENTION

In accordance with the present invention, improved crosslinked water-absorbent resins are prepared by aqueous solution polymerization while dehydrating or drying the reaction product during polymerization by utilizing the exothermic heat from the copolymerization and crosslinking reactions for drying.

In accordance with another important feature the present invention, the water-absorbent resins are surface treated with polyquaternary amines to further substantially and unexpectedly increase the rate of water absorption, amount of water absorption and overall retention of water by the resin. Treatment of the polymer at any time after synthesis and sufficient drying will improve its water absorption properties; however, for economics and ease of manufacture, the surface treatment is most advantageously performed immediately after the polymer is synthesized, dried to an appropriate water content and sized, such as by grinding.

It has been found that acrylic acid, neutralized in the range of 70 to 100 mole percent, will polymerize in the presence of a metal oxide, and crosslink rapidly with a polyvinyl monomer crosslinking agent to drive away excess water leaving a solid, water-absorbing resin having a desired degree of polymerization as well as new and unexpected water-absorption and water-retention properties. One or more polymerization catalysts or initiators can be added to the aqueous monomer mixture to aid in polymerization. As will be discussed more fully hereinafter, subsequent surface treatment with an electrically positive-charged polyquaternary amine serves to further substantially improve the water-absorption and water-retention properties of the water-absorbent resin.

According to the method of the present invention, a hot aqueous mixture comprising acrylic acid neutralized 70 to 100 mole percent; styrene, in an amount of 0% to 25% based on the weight of acrylic acid or acrylate; a metal oxide, in an amount of 0.001% to 5% based on the total weight of the aqueous mixture; a water-miscible or water-soluble polyvinyl monomer; water and, when desired, an organic solvent having a boiling point of 40 to 150° C., and that contains the acrylate monomer; the styrene; the metal oxide; and the polyvinyl monomer in a combined concentration of 30 to 80 wt. %, is prepared.

To achieve the full advantage of the present invention, the acrylate, styrene, metal oxide, and polyvinyl monomers are present in a combined concentration of less that 70 weight percent of the solution. In accordance with another important embodiment of the present invention, the combined concentration of the acrylate, styrene, metal oxide and polyvinyl monomers is less than 55 weight percent of the solution. The concentration of the monomers and metal oxide is deliberately determined considering the state of the solution (i.e., as to whether or not the monomers can be completely dissolved in water), ease of the reaction of the monomers, escape of the monomers due to the spattering during the reaction, and similar process parameters.

The aqueous mixture can be prepared easily, usually by placing acrylic acid, a strong alkali such as potassium hydroxide and/or ammonium hydroxide or a basic amine for neutralizing the acid, the styrene, the metal oxide and the polyvinyl monomer into water in such amounts that the resulting mixture has the above-mentioned monomer and metal oxide concentrations. To thoroughly mix the monomers and the metal oxide, the mixture can be stirred or agitated, and heated to an elevated temperature.

Any strongly basic alkali metal compound can be used for neutralization of the acrylic acid, such as ammoniun hydroxide, potassium hydroxide, sodium hydroxide, lithium hydroxide, cesium hydroxide, ammonium carbonate, potassium carbonate and/or sodium carbonate. Although it is desirable to use the neutralizing agent usually in an amount sufficient to neutralize acrylic acid 100 mole %, it is not necessary to neutralize the acid 100%. However, the neutralizing agent, e.g., hydroxide, is used in such an amount as to achieve not less than about 70% neutralization. Accordingly, the aqueous solution may contain up to about 30 mole percent of free acrylic acid based on the amount of acrylic acid and acrylate. However, a large quantity of free acrylic acid, if present in the aqueous solution, is likely to partly splash out of the reaction vessel, resulting in a loss during the reaction, thereby leading to a reduced degree of polymerization. Using an excessive amount of neutralizing agent will not pose any particular disadvantage, however, the excess neutralizing agent does not participate in the polymerization reaction and is therefore useless.

It also has been found that when the aqueous solution further contains an organic solvent having a boiling point of about 40° C. to about 150° C., the temperature of the aqueous solution is controlled much more easily, and the resulting crosslinked waterabsorbent polymer has a remarkably improved ability to absorb water at an initial rate.

In accordance with the present invention, when incorporating an organic solvent, the aqueous solution has a solidifying point of about 10° C. to about 20° C. lower than solutions absent the organic solvent. Therefore, the allowable range of temperature control is increased by at least about 3 times. The organic solvent is vigorously evaporated together with water by the heat of polymerization of the monomers. Since the latent heat of the evaporation of the organic solvent is considerably smaller than that of water, the organic solvent functions as a blowing agent in the polymerization reaction system, consequently rendering the resulting water-absorbent resin porous. The resin therefore exhibits about 2 to about 5 times higher initial rate of water-absorption than the one obtained without using the organic solvent while possessing high water-absorbing ability. Thus, the organic solvent, when added to the aqueous monomer solution, produces improved effects without in any way impairing the advantages resulting from the use of the monomer solution.

Examples of organic solvents that can be used in the invention when desired have a boiling point of about 40° C. to about 150° C., and include methanol, ethanol, propanol and similar alcohol solvents; acetone, methyl ethyl ketone and similar ketone solvents; cyclohexane, n-hexane, n-heptane and like hydrocarbon solvents; benzene, toluene and like aromatic hydrocarbon solvents; and tetrahydrofuran and like furan solvents. These solvents may be used singly or in admixture. The solvent is used in an amount of 0.5 to 15 wt. %, preferably 1 to 10 wt. %, based on the combined amount of the acrylic acid, styrene, metal oxides and polyvinyl monomers. With less than 0.5 wt. % of the solvent present, a sufficient blowing action will not occur, and the solidifying point of the monomer solution will not be greatly lowered Conversely, if more than 15 wt. % of the solvent is used, the resulting resin is likely to exhibit reduced water-absorbing ability, although achieving a high initial rate of water-absorption Moreover the monomers are likely to separate out from the aqueous solution and therefor affect polymerization. Since the monomer solution is heated prior to polymerization, and because the organic solvent evaporates along with water, the boiling point of the solvent is more preferably in the range of 55° C. to 120° C.

In accordance with the present invention, acrylic acid, neutralized 70–100 mole percent, is mixed with about 0.001% to about 5% of a metal oxide, such as titanium dioxide, based on the total weight of of the aqueous mixture; 0% to 25% styrene, based on the weight of acrylic acid or acrylate; and a watermiscible or water-soluble polyvinyl monomer to form a homogeneous, aqueous mixture at a temperature of about 20 to 100° C. The solution is subjected to a polymerization reaction and a crosslinking reaction by the addition of a polymerization initiator. The polymerization reaction proceeds sufficiently within a very short period of time and if the monomer concentration is at least 30 percent by weight of the homogeneous aqeuous mixture, the heat of the polymerization and crosslinking reactions will evaporate water rapidly from the reaction system to form a dry, solid (less than 15 percent by weight water), water-absorbent resin without the need for any subsequent drying step. The solid can be easily pulverized into a powder suitable for any desired use.

According to an important embodiment of the present invention, a hot, i.e., at least 25° C., aqueous mixture is prepared first including acrylic acid neutralized 70 to 100 mole percent; styrene, in an amount of 0% to 25% by weight, based upon the weight of acrylic acid or acrylate; a metal oxide in an amount of 0.001% to 5% based on the total weight of the aqueous mixture; optionally acrylamide; a water-miscible or water-soluble polyvinyl monomer; and water. The aqueous solution can be prepared easily by placing (A) acrylic acid, and an amine and/or a caustic alkali and/or ammonia for neutralizing the acid; (B) the metal oxide, in an amount of 0.001% to 5% based on the total weight of the aqueous solution; (C) acrylamide (0–30 mole percent based on acrylic acid); (D) styrene, 0–25% by weight based upon the weight of acrylic acid or acrylate; and (E) a polyvinyl monomer into water to form a mixed monomer mixture. To dissolve the monomers thoroughly, the mixture can be heated to an elevated temperature up to the boiling point of water, i.e., 100° C. To maintain a homogeneous mixture, the mixture can be continuously stirred or agitated.

The polyvinyl monomer to be used in accordance with the present invention should be miscible with or soluble in water so that the polyvinyl monomer will be uniformly dissolved or dispersed in the aqueous solution of the monomer mixture. Examples of such polyvinyl monomers include trimethylolpropane triacrylate; bisacrylamides such as N,N'-methylenebisacrylamide and N,N'-methylenebismethacrylamide; polyacrylic (or polymethacrylic) acid esters represented by the following formula (I); and diacrylamides represented by the following formula (II). Among these, especially preferably are N,N'-methylenebisacrylamide, N,N'-methylenebismethacrylamide and like bisacrylamides.

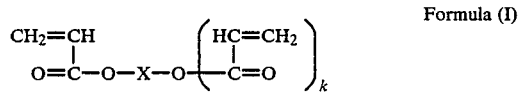

Formula (I)

wherein X is ethylene, propylene, trimethylene, hexamethylene, 2—hydroxypropylene, $(CH_2CH_2O)_nCH_2CH_2$— or

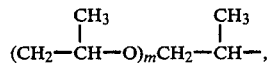

n and m are each an integer of from 5 to 40, and k is 1 or 2.

The compounds of the formula (I) are prepared by reacting polyols, such as ethylene glycol, propylene glycol, trimethylolpropane, 1,6-hexanediol, glycerin, pentaerythritol, polyethylene glycol and polypropylene glycol, with acrylic acid or methacrylic acid.

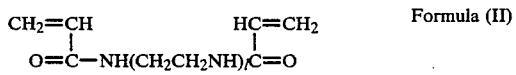

Formula (II)

wherein l is 2 or 3.

The compounds of the formula (II) are obtained by reacting polyalkylenepolyamines, such as diethylenetriamine and triethylenetetramine, with acrylic acid.

The polyvinyl monomer is used in an amount of about 0.001 to 0.6 wt. % based on the amount of the acrylic acid, styrene and acrylamide monomers and the metal oxide in the aqueous monomer mixture. In accordance with an important embodiment of the present invention, the polyvinyl monomer crosslinking agent should be present in the aqueous solution in an amount of at least 0.2 wt. % based on the total weight of monomers and the metal oxide to provide a resin sufficiently crosslinked to have a "dry feel" after significant water-absorption. If the polyvinyl monomer is included in the aqueous solution in an amount of 0.2 to 0.6 weight percent based on the weight of neutralized acrylic acid, styrene, metal oxide, and polyvinyl monomers, the resulting polymer will have an exceedingly "dry feel" on absorption of water.

The metal oxides used in accordance with the present invention are essentially insoluble in water. However with sufficient stirring or agitation, the metal oxide will remain homogeneously dispersed throughout the aqueous mixture. The metal oxide does not copolymerize with the neutralized acrylic acid, styrene, acrylamide and/or polyvinyl monomer; however, the metal oxide is physically incorporated and included, essentially non-covalently, throughout the crosslinked acrylate polymer. The homogeneous incorporation of the metal oxide throughout the crosslinked acrylate polymer surprisingly and unexpectedly results in improved water-absorption and improved water-retention by the polyacrylate polymer.

The metal oxides that are useful in the present invention are essentially non-reactive metal oxides that are essentially insoluble in the aqueous monomer mixture. Often it is desirable that the metal oxide is white in color such that the resulting acrylate resin, containing the metal oxide, is white in color. However, a colored metal oxide can be used to make a colored polyacrylate resin when such color is desired or is not offensive. Exemplary metal oxides, both white and colored, include titanium dioxide, magnesium oxide, zinc oxide, barium oxide, zirconium oxide, calcium oxide, silicon dioxide, aluminum oxide, selenium dioxide, tin oxide, bismuth oxychloride, antimony trioxide, antimony pentoxide, beryllium oxide, cadmium oxide, cerium oxide, iron oxide, lead oxide, bismuth oxide, vanadium oxide, cobalt oxide, or mixtures thereof. It is also envisioned that multiple metal oxides, such as magnesium aluminum oxide, zinc aluminum oxide, magnesium titanium oxide, iron titanium oxide, calcium titanium oxide, beryllium aluminum oxide, or mixtures thereof, can be used in the method of the present invention. In addition, the metal oxides and multiple metal oxides can be used in combination. Furthermore, the above-mentioned metal oxides and multiple metal oxides are merely listed as examples of oxides that can be used in accordance with the method of the present invention, and these examples are not intended to limit the scope of the oxides that can be used according to the method of the present invention. The metal oxides are incorporated into the water-absorbent resins of the present invention in the form of powders, generally ranging from approximately 10u (microns) to approximately 200u in diameter, and in particular ranging from approximately 50u to approximately 125u in diameter.

In addition, the metal oxides that are useful in the method of the present invention can be hydrated or anhydrous. Furthermore, the particular crystal structure of the metal oxide is not critical. For example, the alpha, beta and gamma forms of aluminum oxide; the hydrated forms of aluminum oxide, such as $Al_2O_3 \cdot H_2O$, $Al_2O_3 \cdot 2H_2O$, and $Al_2O_3 \cdot 3H_2O$; the hydrated forms of titanium dioxide, like $TiO_2 \cdot H_2O$ and $TiO_2 \cdot 2H_2O$; hydrated and anhydrous silicon dioxide; or mixtures thereof can be used in the method of the present invention. However, as previously described, other metal oxides and multiple metal oxides also can be used in accordance with the method of the present invention, as long as the resulting polyacrylate resin exhibits the improved water-absorption and water-retention properties observed when using a metal oxide such as titanium dioxide.

It has been found that the particular metal oxide used to improve the water-absorption and water-retention properties of the acrylate polymers may vary according to the particular end use of the acrylate polymer. For example, if a white polymer is required, as in a disposable diaper, a white metal oxide, like titanium dioxide, is preferred in order to enhance customer appeal. However, for other applications, such as water retaining agents or dehydrating agents, colored polymers may be preferred for esthetic purposes, and therefore colored metal oxides can be utilized in the method of the present invention. Regardless of the color of the metal oxide, in all cases the metal oxide is essentially non-reactive with the monomers of the aqueous monomer mixture and the resulting water-absorbent polymer such that ionic crosslinking between the pendant groups of the polymer does not occur. In addition, the metal oxide should be dispersed homogenously throughout the monomer mixture to ensure homogeneous incorporation and inclusion of the metal oxide in the polyacrylate resin.

The metal oxide improves the color and improves the water-absorption and water-retention of the polyacrylate polymer when the metal oxide, on an anhydrous metal oxide basis, is present in the aqueous monomer mixture from about 0.001% to about 5%, based upon the total weight of the aqueous monomer mixture. To achieve the full advantage of the present invention, the metal oxide is present in the aqueous monomer mixture from about 0.75% to about 3% based upon the total weight of the aqueous monomer mixture.

In accordance with the method of the present invention, the aqueous mixed monomer and metal oxide mixture is heated and thereafter subjected to polymerization and crosslinking reactions with the addition of a polymerization initiator. Although the temperature of the aqueous mixed monomer and metal oxide mixture is not particularly limited since the polymerization of the monomers in solution is initiated by the addition of the initiator, the temperature is usually about 50° C. to about 85° C., preferably about 60° C. to about 75° C.

The method of the present invention is distinguished from the method disclosed by Makita et al. in U.S. Pat. No. 4,587,308, wherein the water-absorbing properties of a water-absorbent polymer are improved by further crosslinking a crosslinked absorbent polymer, through the pendant carboxyl moieties of the polymer, in the presence of an inert inorganic powder such as titanium dioxide. In contrast to the method of the present invention, wherein the metal oxide is added to the aqueous mixed monomer solution before polymerization is initiated, the Makita method teaches adding the inert inorganic powder to an aqueous mixture of the absorbent polymer, containing pendant carboxy groups, and a crosslinking agent like a diglycidyl ether, to further covalently crosslink the absorbent polymer through the pendant carboxyl groups. According to the method of Makita, the inert inorganic powder is added to disperse the polymer particles and prevent aggregation and lumping of the polymer particles in order to permit uniform crosslinking; Makita does not teach or suggest that the inert inorganic powder is added to increase the water-absorption and water-retention of the polyacrylate resin.

The method of the present invention also is distinguishable from the composition disclosed by Evani et al in U.S. Pat. No. 4,535,098. Evani disclosed a water-absorbent polymer composition including a major portion of water-soluble monomers and minor portions of a water-insoluble monomer having a pendant hydrophobic moiety that are polymerized in the presence of a micelle-forming surfactant. The composition optionally can include a crosslinking agent and a colloidal support and/or a filler to improve the gel strength of the composition. The colloidal support, such as fumed silica, alumina, titania and colloidal oxide sols of zinc, zirconium, nickel, iron and cobalt, have a particle diameter of about 50 Å (Angstroms) to about 200 Å to yield transparent fluids. The filler is non-colloidal and is similarly used to improve gel strength of the polymer. However, in accordance with the present invention, metal oxides of a significantly larger diameter, generally ranging in particle size from about 10u (10 × $10^4$ Å) to about 200u (200 × $10^4$ Å), are utilized both to improve the water-absorption and water-retention properties of the crosslinked polyacrylate resin, and to impart opacity or color to the water-absorbent resin as opposed to translucence.

In accordance with the method of the present invention, various polymerization initiators that are known for use in preparing polyacrylates, can be used. Examples of useful initiators are redox initiators comprising a reducing agent, such as a sulfite or bisulfite of an alkali metal, ammonium sulfite, ammonium metabisulfate or ammonium bisulfite, 3,3'3''-nitrilotrispropionamide, a persulfate of an alkali metal or ammonium persulfate, L-ascorbic acid, ferrous salts, or sodium bromate; t-butyl hydroperoxide; benzoyl peroxide; di-t-butyl hydroperoxide; t-butyl perbenzoate; dicumyl peroxide; t-butyl peroxy isopropyl carbonate; diisopropyl benzene hydroperoxide; caprylyl peroxide; t-butyl diperphthalate; sodium peracetate; and 1,1-di-t-butylperoxy-3,3,5-trimethylcyclohexane. Examples of suitable thermal initiators include azobisisobutyronitrile; 4-t-butylazo-4'-cyanovaleric acid; 4,4'-azobis(4-cyanovaleric acid); 2,2'-azobis(2-amidinopropane)dihydrochloride; 2,2'-azobis(2,4-dimethylvaleronitrile); dimethyl 2,2'-azobisisobutyrate; 2,2'-azobis(2,4-dimethylvaleronitrile); (1-phenylethyl)azodiphenylmethane; 2,2'-azobis(2-methylbutyronitrile); 1,1'-azobis(1-cyclohexanecarbonitrile); 2-(carbamoylazo)-isobutyronitrile; 2,2'-azobis(2,4,4-trimethylpentane); 2-phenylazo-2,4-dimethyl-4-methoxyvaleronitrile; 2,2'-azobis(2-methylpropane); 2,2'-azobis(N,N'-dimethyleneisobutyramidine)dihydrochloride; 4,4'-azobis(4-cyanopentanoic acid); 2,2'-azobis(2-methyl-N-[1,1-bis(hydroxymethyl)-2-hydroxyethyl]propionamide); 2,2'-azobis(2-methyl-N-[1,1-bis(hydroxymethyl)ethyl]propionamid 2,2'-azobis[2-methyl-N-(2-hydroxyethyl)propionamide]; 2,2'-azobis(isobutyramide)dihydrate and the like.

These initiators, redox and thermal, can be used singly or in a suitable combination. Of these, especially preferable are a redox initiator composed of ammonium persulfate and sodium hydrogen sulfite, and azo initiators such as azobisisobutyronitrile and 2,2'-azobis(2-amidinopropane)dihydrochloride. The initiators are advantageously used usually in the form of an aqueous solution, but can be used as diluted with a suitable solvent. The initiator is used in a usual amount, i.e., in an amount, calculated as solids, of about 0.1 to about 10%, preferably about 0.5 to about 5%, of the combined weight of the monomers, namely acrylate (and free acrylic acid); acrylamide; styrene; and polyvinyl monomer crosslinking agent. Depending on the amount and kind of the initiator, the initiator is usable together with isopropyl alcohol, alkyl mercaptan or other chain transfer agents to control the molecular weight of the polyacrylate copolymer to be obtained.

When a thermal and redox initiator are used in combination, the temperature of the aqueous mixed monomer and metal oxide mixture can vary considerably prior to the addition of the thermal and redox initiators, depending upon the particular thermal initiator added. In any event, the initial temperature of the aqueous mixed monomer and metal oxide mixture should be below the thermal decomposition temperature of the initiator or substantial polymerization initiation results; and the temperature of the mixed monomer and metal oxide mixture should be high enough that the redox initiator causes sufficient polymerization at the initial temperature of the monomer solution to raise the temperature of the aqueous mixed monomer and metal oxide mixture to a level sufficient that the thermal initiator, together with the redox initiator, causes substantially complete polymerization leaving less than about 1000 PPM free monomer, and generally less than about 500 PPM free monomer. Free monomer levels less than 200 PPM and even less than 100 PPM have been achieved in accordance with the process of the present invention. The combination of initiators can be added to the mixed monomer-metal oxide mixture in a batch process or continuously.

In accordance with an important feature of the present invention, it has been found that a combination of at least one thermal initiator with at least one redox initiator enables efficient polymerization while limiting the free acrylic acid and acrylate monomer content to less than 1000 ppm, and generally less than 500 PPM in the completed water-absorbing polymer.

By the addition of the polymerization initiator, the mixed monomer-metal oxide mixture is subjected to polymerization with evaporation of water without heating the system from outside. More advantageously, the reaction is carried out by admixing a predetermined amount of the initiator or an aqueous solution thereof with the stirred or agitated mixed monomer metal oxide mixture and causing the resulting mixture to flow down onto and spread over a traveling conveyor belt or reacted continuously. The initiator can be added to the mixed monomer-metal oxide mixture as it is poured onto the conveyor belt.

The copolymerization proceeds rapidly after admixing the initiator with the mixed monomer-metal oxide mixture and is completed within a short period of time, usually in about 30 seconds to about 10 minutes. This rapid reaction of the homogenously mixed monomer and metal oxide mixture assures that the metal oxide is homogeneously dispersed throughout the resulting water-absorbent polymer. In addition, the reaction is exothermic, so that the reaction system is rapidly heated to about 100 to about 130° C. by the heat of polymerization. Consequently, particularly where the monomer concentration in the aqueous mixture is at least 50 percent by weight, the water evaporates from the system rapidly to give a relatively dry, solid copolymer of low water content without resorting to any external heating. The water content of the copolymer is usually up to about 15%, and generally about 8 to 12% by weight as recovered. Subsequently, the dry solid copolymer can be made into the desired powder easily by a usual method, for example by pulverization, without a drying step.

The powder thus obtained has outstanding water-absorbing ability and is useful for sanitary goods, paper diapers, disposable diapers and like hygenic goods, agricultural or horticultural water-retaining agents, industrial dehydrating agents, sludge coagulants, thickening agents, condensation preventing agents for building materials, release control agents for chemicals and various other applications.

In accordance with another important feature of the present invention, it has been found that surface treatment of a water-absorbent resin including a metal oxide, with a polyquaternary amine, further substantially and unexpectedly increases the water-absorbent qualities of the resin while retaining the necessary "dry feel" of the resin. In a preferred method, the polyquaternary amine surface treatment is performed immediately following the polymerization, drying and sizing steps. To achieve the full advantage of the present invention, the polyquaternary amine is dispersed in a suitable solvent to produce a solution containing from about 0.1% to about 20% polyquaternary amine by weight. Suitable solvents include liquids capable of solubilizing the polyquaternary amine and of rapid and complete evaporation. Such solvents include the lower alcohols, especially methanol or isopropyl alcohol; lower ketones, such as acetone or methyl ethyl ketone; and other such low molecular weight organic solvents. Water is not a recommended solvent due to its low evaporation rate and its absorption by the water-absorbent resin, while methanol has been found to be the most advantageous polyquaternary amine diluent.

The polyquaternary amine-methanol solution is evenly sprayed onto the surface of the water-absorbent resin, followed by a blending operation to attain a uniform coating of the polyquaternary amine on the surface of the polymer. After blending and methanol evaporation, the water-absorbent resin is thereby surface coated with 0.1% to 5.0% (by dry weight) of a polyquaternary amine. It is not essential to treat the water-absorbent resin immediately after synthesis and drying, since surface treatment of the waterabsorbent polymer at any time prior to use will yield the new and unexpected results described herein.

Polyquaternary amines are readily available products from a number of commercial sources. The actual chemical structure of the polyquaternary amine will depend upon the starting materials used to synthesize the polyquaternary amine, with the diversity of available starting materials leading to polyquaternary amines of quite diverse structure. Among the various polyquaternary amines available are condensation products of hexamethylenediamine, dimethylamine, and epichlorohydrin; condensation products of dimethylamine and epichlorohydrin; copolymers of hydroxyethyl cellulose and diallyldimethyl ammonium chloride; copolymers of acrylamide and beta-methacrylyloxyethyl trimethyl ammonium chloride; hydroxyethyl cellulose reacted with epichlorohydrin, then quaternized with trimethylamine; or homopolymers of diallyldimethyl ammonium chloride. Polyquaternary amines may also be synthesized by the reaction of dimethyl sulfate with polymers such as polyethyleneimines, copolymers of vinyl pyrolidone and dimethylaminoethyl methacrylate, or copolymers of ethyl methacrylate, abietyl methacrylate and diethylaminoethyl methacrylate. Regardless of the overall chemical structure, each of the polyquaternary amines possesses the positively-charged ammonium nitrogen atom required for interaction with the negatively-charged moiety of the water-absorbent polymer.

The polyquaternary amines are available in a wide molecular weight range, however, for the present invention the preferred molecular weight of the polyquaternary amine ranges from about 200 to about 5000. To achieve the full advantage of the present invention, the molecular weight range of the polyquaternary amine is between about 300 and about 4000. Suitable polyquaternary amines are exemplified by the following tradename products:

MAGNIFLOC 577C from American Cyanamid Co.;
MAGNIFLOC 579C from American Cyanamid Co.;
MAGNIFLOC 581C from American Cyanamid Co.;
MIRAPOL WT from National Chemical Co., Inc.;

RETEN 205 from Hercules, Inc.;
RETEN 210 from Hercules, Inc.;
RETEN 220 from Hercules, Inc.;
UCARE Polymer JR-30M from Union Carbide Corp.;
UCARE Polymer JR-125 from Union Carbide Corp.;
GAFQUAT 734 from GAF Corp.; and
GAFQUAT 755 from GAF Corp.
However, other polyquaternaries can be used in the present invention.

In accordance with a new and unexpected feature of the present invention, it has been found that by polymerizing partially neutralized or fully neutralized acrylic acid in the presence of a metal oxide, such as titanium dioxide, the total absorbency of the resulting polymer as well as the retention capacity of the polymer is unexpectedly superior to the absorbent polymer made without the metal oxide. Further, in accordance with another new and unexpected feature of the present invention, when the metal oxide is included in the aqueous monomer mixture in an amount of about 0.001% to about 5% based on the total weight of the aqueous monomer mixture, the initial rate of the water-absorption of the resulting copolymer is unexpectedly superior to the acrylate polymer manufactured absent the metal oxide. Furthermore, it is seen that adding the metal oxide to the monomer solution in an amount of about 0.001% to about 5% based on the total weight of the aqueous monomer mixture, also increases the total water-absorption and total water retention of the polymer. Unexpectedly, the total water-absorption and the total water-retention is further increased when the polymer including the metal oxide is surface treated with a polyquaternary amine.

In order to show the new and unexpected results achieved by the polymerization of partially or fully neutralized acrylic acid in the presence of a metal oxide, the water-absorption and retention properties of an acrylic acid homopolymer were studied and compared to the water-absorption and retention properties of a polyacrylate including a metal oxide. The crosslinked acrylic acid homopolymer was prepared, and surface treated, in the same manner as described hereinafter in Example 1 using the following mixed monomer solution:

| CHEMICAL | PARTS BY WEIGHT | PERCENT |
| --- | --- | --- |
| Acrylic Acid | 16.80 | 54.15 |
| Ammonium hydroxide (30% aqueous ammonia) | 4.20 | 13.54 |
| Potassium hydroxide | 4.20 | 13.54 |
| Azo crosslinking agent | 0.13 | 0.42 |
| GPTA (glycerol propoxy triacrylate molecular weight 428.5) | 0.002 | 0.01 |
| Ammonium carbonate | 3.31 | 10.67 |
| Water | 2.30 | 7.67 |
| TOTAL | 30.94 | 100.00 |

To demonstrate the new and unexpected results achieved by including a metal oxide in the monomer mixture, acrylate polymers were synthesized in the presence of about 2% by weight of a metal oxide (based upon the total weight of the monomer mixture) in the same manner as described hereinafter for the crosslinked polymer of acrylic acid. In each case, the polymer, either partially or fully neutralized, was tested in its untreated form and was tested after treatment with a polyquaternary amine.

The metal-oxide containing polymers made according to the method of the present invention were compared to homoacrylate polymers synthesized in the absence of metal oxides and also compared to acrylatestyrene copolymers, with and without incorporated metal oxides, for their water-absorption and water-retention capabilities. For the polymers that were treated with a polyquarternary amine, the polymer was treated with MAGNIFLOC 579C, a polyquaternary amine with highly cationic properties and of moderate, e.g., 2000–4000, molecular weight.

For example, an acrylic acid-styrene copolymer was prepared in the same manner as the acrylic acid homopolymer described above, except for the addition of styrene by copolymerizing the following mixed monomer composition:

| CHEMICAL | PARTS BY WT. | PERCENT |
| --- | --- | --- |
| Acrylic Acid | 16.96 | 53.28 |
| Ammonium Hydroxide (30% aqueous ammonia) | 4.20 | 13.20 |
| Potassium hydroxide | 4.20 | 13.20 |
| Styrene | 0.65 | 2.04 |
| 4-t-butylazo-4'-cyanovaleric acid | 0.13 | 0.41 |
| GPTA (glyceryl propoxytriacrylate) MW = 428.5 | 0.002 | 0.01 |
| Ammonium carbonate | 3.31 | 10.40 |
| Water | 2.38 | 7.49 |
| TOTAL | 31.83 | 100.00 |

When the mixed monomer solution includes styrene, the resulting copolymer demonstrates increased total water-absorbency and an increased total amount of water retained. These results demonstrate the positive effect on water-absorbency and water-retention of copolymerizing styrene with neutralized acrylic acid. Surprisingly and unexpectedly, when a metal oxide, such as titanium dioxide, also is present in the monomer solution, further improved water-absorption and water-retention properties compared to the polymers that do not include the metal oxide are achieved. Such results are unexpected due to the already high water-absorbent capabilities of the polyacrylate resin and the inherent inability of metal oxides, like titanium dioxide, to absorb liquids at all.

It was demonstrated that a neutralized polyacrylic acid including 2% by weight titanium dioxide based on the total weight of the monomer mixture showed a moderate 4% increase in total water absorption compared to a neutralized polyacrylate resin absent the titanium dioxide; and surprisingly and unexpectedly also showed a 2% increase in total water-retention compared to a neutralized polyacrylate resin absent the titanium dioxide. Such an increase in total water retention improves the "dry feel" of the polymer after water absorption. Furthermore, surface-treating the titanium dioxide-containing polymer with 0.2% by weight of a polyquaternary amine showed a further improvement in total absorbence for a 4% improvement over the neutralized and untreated polyacrylic acid and a 4% improvement over the neutralized and untreated titanium dioxide-containing polyacrylate; and a further total water-retention improvement of 2% over the neutralized and untreated polyacrylic acid and a 2% improvement over the neutralized and untreated titanium dioxide-containing polyacrylate.

Similarly, an improvement is achieved by including 2% of titanium dioxide in the copolymerization of styrene and neutralized acrylic acid compared to copolymerizing styrene and neutralized acrylic acid in the absence of the metal oxide. For example, including 2% by weight titanium dioxide based on the total weight of the monomer mixture in a styreneacrylic acid copolymer showed a 3% increase in total water absorption compared to a 2% styrene copolymer without titanium dioxide and a 3% increase compared to a 4% styrene copolymer without titanium dioxide. In addition, a significant increase in total water-retention of 2% and 2%, respectively, was demonstrated.

Improved water absorption and water-retention results also are observed for polyacrylates including 2% by weight titanium dioxide based on the weight of acrylic acid; 2% titanium dioxide both in the presence and absence of styrene; and for a polyacrylate including 1% titanium dioxide. For each polymer, surface treatment with a polyquaternary amine further improved the water absorption and water-retention of the polymers.

In addition, the polyacrylate water-absorbent resins were tested subjectively for dry feel. Polyacrylate resins including a metal oxide were compared to polyacrylate resins absent a metal oxide by allowing one-half gram of the resin to contact 15 ml of a 1% aqueous sodium chloride solution. A panel of ten experts then rated the wetted resins for dry feel, and ranked the wetted resins on a scale of from 1 to 5. In this test, the experts apply pressure to the resin, then rank the resins for "dry feel". The "dry feel" rating is directly related to total water retention capability of the water-absorbent resin. Practically, this test is analogous to a diapered child sitting on a soaked diaper. The ranking is an indication of the amount of liquid the diaper will retain when subjected to the weight of the sitting child. The amount of liquid retained by the diaper material is important in regard to eliminating liquid leakage from the diaper and in regard to the ultimate discomfort felt by the child due to skin contact with nonretained liquid. Surprisingly and unexpectedly, the metal oxide-containing polymers demonstrated a dry feel rating of 4 compared to a dry feel rating of 2.5 to 3 for an essentially identical polymer that does not include a metal oxide. Such a signficant increase in "dry feel" rating demonstrates the improved ability of metal-oxide containing water-absorbent resins to retain absorbed liquid under pressure.

The present invention, utilizing metal oxidecontaining polyacrylate resins is described in greater detail with reference to the following examples.

EXAMPLE 1

The following ingredients are combined, wherein percents are weight percents based on the total weight of the monomer mixture formed, unless otherwise noted, 48.01% acrylic acid and 2% titanium dioxide, first are thoroughly admixed, then 30.66% of aqueous potassium hydroxide (53.2% KOH) and 11.82% potassium carbonate, serving as neutralizing agents, are added. Thereafter 0.02% of N,N-methylenebisacrylamide, as a polyvinyl monomer, is added to prepare an aqueous mixture of potassium acrylate, having a neutralization degree of about 80%, and titanium dioxide. The combined monomer-metal oxide concentration is about 70 wt. %.

The aqueous mixture is stirred and is maintained at 70° C., and with the mixture is admixed 0.36% of 2,2'-azobis-(2-amidino-propane)dihydrochloride and 0.20% of ammonium persulfate both in an aqueous solution. The final solution is as follows:

| CHEMICALS | |
| --- | --- |
| Acrylic Acid | 48.01% |
| Titanium Dioxide | 2.00% |
| Potassium Hydroxide | 16.31% |
| Potassium Carbonate | 11.82% |
| N,N-Methylenebisacrylamide | 0.02% |
| Azo Polymerization Initiators | 0.36% |
| Ammonium Persulfate | 0.20% |
| Water | 21.28% |
| TOTAL | 100.00 |

The stirred mixture is poured onto a traveling endless belt and spread thereover in the form of a layer about 10 mm (millimeters) in thickness. The reaction then is initiated by adding 0.14% by weight of an aqueous solution containing 33% by wt. of a 50/50 mixture of sodium thiosulfate and ammonium persulfate redox initiators to the monomer/metal oxide mixture. About 30 seconds thereafter, the mixture starts to polymerize, and the reaction is completed in about 1 minute. The maximum temperature of the mixture during the reaction is about 120° C.

The polymer is allowed to complete curing for about 30 minutes at ambient temperature to give a dry solid strip of potassium polyacrylate incorporating the titanium dioxide, and having a water content of 1% and a residual monomer concentration of less than 1000 ppm. The solid strip of polymer is pulverized into a powder, then surface treated by evenly spraying a methanol solution containing from about 5% by weight of a polyquaternary amine over the powder until it is surface treated with from about 0.6% of the polyquaternary amine by dry weight. A separate blending operation, or the packaging operation, serves to evenly distribute the surface-treated resin throughout the product. An identical surface-treating procedure is used for crosslinked homopolymers of acrylic acid and the crosslinked copolymers of acrylic acid with styrene, acrylamide or other ethylenically-unsaturated monomers by evenly spraying a methanol solution containing from about 0.1% to about 20% by weight of a polyquaternary amine over the powder until it is surface treated with from about 0.1% to about 5% of the polyquaternary amine by dry weight.

EXAMPLES 2 to 5

Polymers are prepared in the same manner as described in Example 1 with the exception of varying at least one of the combined concentration of monomers, the amount of polyvinyl monomer (N,N-methylenebisacrylamide), the kind and amount of metal oxide, the kind and amount (degree of neutralization) of neutralizing agent, and the amounts based on the combined amount of the monomers of azo polymerization initiator. Onehalf of the polymerized polymer solid was surface-treated as in Example 1, and one-half was left untreated. The following compositions are polymerizable:

EXAMPLE 2

| | |
|---|---|
| Acrylic Acid | 47.90% |
| Titanium Dioxide | 4.00% |
| Potassium Hydroxide | 16.26% |
| Potassium Carbonate | 11.80% |
| N,N-methylenebisacrylamide | 0.02% |
| Azo Polymerization Initiator | 0.36% |
| Ammonium Persulfate | 0.20% |
| Water | 19.46% |
| TOTAL | 100.00% |

EXAMPLE 3

| | |
|---|---|
| Acrylic Acid | 49.46% |
| Silicon Dioxide | 2.00% |
| Potassium Hydroxide | 11.25% |
| Potassium Carbonate | 15.01% |
| N,N-methylenebisacrylamide | 0.023% |
| Azo Polymerization Initiator | 0.36% |
| Ammonium Persulfate | 0.20% |
| Water | 21.70% |
| TOTAL | 100.00% |

EXAMPLE 4

| | |
|---|---|
| Acrylic Acid | 57.95% |
| Aluminum Oxide | 2.00% |
| Potassium Hydroxide | 14.51% |
| Ammonium Carbonate | 11.61% |
| GPTA | 0.02% |
| Azo polymerization initiator | 0.24% |
| Ammonium hydroxide (30% wt. aqueous) | 13.67% |
| TOTAL | 100.00% |

EXAMPLE 5

| | |
|---|---|
| Acrylic Acid | 57.27% |
| Calcium Oxide | 2.00% |
| Potassium Hydroxide | 14.35% |
| Ammonium Carbonate | 11.48% |
| N,N-methylenebisacrylamide | 0.11% |
| Azo Polymerization Initiator | 0.14% |
| Ammonium hydroxide (30% wt. aqueous) | 14.65% |
| TOTAL | 100.00% |

The amount of polyvinyl monomer listed is expressed in % by weight based on the combined amount of potassium acrylate, free acrylic acid, styrene and the polyvinyl monomer, and the concentration of initiator is expressed in % by weight based on the combined amount by weight (calculated as solids) of the monomers and the initiator, the same as hereinbefore.

EXAMPLE 6

To 22.2 g of deionized water, 71.1 g of acrylic acid and 1.0 g of titanium dioxide are added first; then 49.5 g of potassium hydroxide having a purity of 85% and serving as a neutralizing agent is added; and thereafter 0.01 g of N,N-methylenebisacrylamide is added as a polyvinyl monomer to prepare an aqueous mixture of potassium acrylate, having a neutralization degree of 75%, and titanium dioxide having a combined concentration of acrylate and metal oxide of about 75% by wt.

The aqueous mixture is maintained at 70° C., and with the solution is admixed 2.9 g of 18% aqueous solution of ammonium persulfate (0.67 wt. % based on the combined weight of the potassium acrylate, free acrylic acid, titanium dioxide and N,N-methylenebisacrylamide). The mixture is poured onto a traveling endless belt and spread thereover in the form of a layer about 10 mm in thickness. About 30 seconds thereafter, the mixture starts to polymerize, and the reaction is completed in about 1 minute. The maximum temperature of the mixture during the reaction is about 120° C.

The reaction gives a dry solid strip of crosslinked potassium polyacrylate homopolymer incorporating the titanium dioxide. The strip is made into a powder by a pulverizer; then surface treated with a 7% methanol solution of a polyquaternary amine to yield a polymer having a 0.3% polyquaternary surface treatment.

EXAMPLES 7 to 10

Polymers are prepared in the same manner as in Example 6 with the exception of changing at least one of the amount of N,N-methylenebisacrylamide and the kind and amount of the polymerization initiator as listed in Table 1 below.

TABLE 1

| Ex. No. | Initiator Kind | Conc. | Amt. of Polyvinyl Monomer |
|---|---|---|---|
| 7 | 2,2'-azobis-(2-amidino-propane) dihydrochloride | 0.5 | 0.01 |
| 8 | 2,2'-azobis-(2-amidino-propane) dihydrochloride | 0.5 | 0.02 |
| 9 | 2,2'-azobis-(2-amidino-propane) dihydrochloride | 1.0 | 0.01 |
| 10 | 2,2'-azobis-(2-amidino-propane) dihydrochloride | 1.0 | 0.02 |

EXAMPLES 11 to 18

Polymers are prepared in the same manner as in Example 1 except that the compounds listed in Table 2 below are used as polyvinyl monomers in the listed amounts.

TABLE 2

| Ex. No. | Polyvinyl Monomer Kind | Amount |
|---|---|---|
| 11 | Ethylene glycol diallyl ester | 0.01 |
| 12 | Ethylene glycol diallyl ester | 0.02 |
| 13 | Diethylenetriaminediacrylamide | 0.01 |
| 14 | Diethylenetriaminediacrylamide | 0.02 |
| 15 | N,N-methylene-bismethacrylamide | 0.01 |
| 16 | N,N-methylene-bismethacrylamide | 0.05 |
| 17 | Polyethylene glycol diacrylate* | 0.01 |
| 18 | Polyethylene glycol | 0.05 |

TABLE 2-continued

| Ex. | Polyvinyl Monomer | |
|---|---|---|
| No. | Kind | Amount |
| | diacrylate* | |

*Polyethylene glycol diacrylate used in Examples 17 and 18 is represented by the following formula:

$$CH_2=CH \qquad CH=CH_2$$
$$| \qquad\qquad\qquad |$$
$$O=C-(OCH_2CH_2)_{20}O-C=O$$

EXAMPLES 19 to 22

Acrylic acid (71.1 g), 5 g of deionized water, 40.9 g of solid potassium hydroxide (water content 4%), 1 gram titanium dioxide and 5.2 g acetone (5 wt. % based on the monomers) are mixed together, and the mixture is continually stirred and is maintained at 75° C. Into the mixture is further admixed 4.0 g of 10% aqueous solution of 2,2'-azobis(2-amidinopropane)dihydrochloride. The resulting mixture is immediately poured onto a traveling endless belt and spread thereover to a thickness of 5 mm. About 15 seconds later, the mixture starts to polymerize, and the polymerization is completed in about 30 seconds. The maximum temperature of the mixture during the reaction is 130° to 135° C.

The reaction gives a dry strip of crosslinked potassium polyacrylate product containing the titanium dioxide. The product is pulverized to a powder 20 to 100 mesh in particle size. The polymer was not surface treated.

The same procedure as above is repeated with use of the other solvents.

EXAMPLE 23

An aqueous monomer mixture is prepared in the same manner as in examples 19 to 22 with the exception of not using any organic solvent and using 10 g of deionized water. The solution is thereafter subjected to polymerization in the same manner as in these examples to obtain a powder of dry solid, that was subsequently surface treated.

EXAMPLES 24 and 26

Water-absorbing resin solids are prepared in the same manner as in Example 19 with the exception of using 3, 5 or 10 wt. %, based on the monomers and titanium dioxide, of methanol in place of 5.2 g of acetone and varying the amount of deionized water so that the combined amount of the water and the methanol is 10 g.

EXAMPLE 27

89.4 gr. of acrylic acid and 9.9 gr. of acrylamide are dissolved in 118.8 gr. of distilled water and 52.6 gr. of KOH is added for 75 mole percent partial neutralization of acrylic acid. One gram of titanium dioxide is added to the solution. 0.018 gr. of N,N'-methylenebisacrylamide is added as the polyvinyl monomer, and 0.08 gr. of ammonium persulfate and 0.08 gr. of sodium thiosulfate are added as the polymerization initiators. The initial temperature of the mixed monomer mixture is 30° C. After polymerization, the solid was surface treated to yield a 0.6% by wt. surface-treated product

EXAMPLE 28

47.1 gr. of acrylic acid and 11.9 gr. of acrylamide are dissolved in 252.1 gr. of distilled water and 27.4 gr. of aqueous ammonia is added for 70 mole percent partial neutralization of acrylic acid. In this case, the concentration of the ammonia is 29 weight percent. In addition, 1 gram of titanium dioxide and 0.006 gr. of N,N'-methylenebisacrylamide are added. The polymerization is performed with the addition of 0.048 cr. of ammonium persulfate and 0.048 gr. of sodium thiosulfate for initiation. In this case, the initial temperature of the mixed monomer solution is 30° C.

EXAMPLE 29

51.9 gr. of acrylic acid and 17.3 gr. of acrylamide are dissolved in 25 gr. of distilled water and they are partially neutralized 80 mole percent with the addition of 32.8 gr. of KOH. One gram of titanium dioxide and 0.007 gr. of N,N'-methylenebisacrylamide is added. For the polymerization catalyst 0.7 gr. of 2,2'-azobisisobutyronitrile dissolved in 10 cc. of acetone is added. The solution is kept at 80° C. in a TEFLON coated, glass fiber reaction chamber until completion of polymerization and crosslinking reactions yielding a solid resin. The resin is then surface treated with a polyquaternary amine.

EXAMPLE 30

17.3 gr. of acrylamide is dissolved in 52.0 gr. of acrylic acid and partial (70 mole percent) neutralization of acrylic acid is accomplished by the addition of 30 gr. of aqueous ammonia having a concentration of 29 weight percent. In this case, for the polyvinyl monomer, 0.007 gr. of N,N'-methylenebisacrylamide is added. One gram of titanium dioxide is added and as the catalyst for copolymerization, 0.7 gr. of 2,2'-azobis(2-amidinopropane)dihydrochloride dissolved in 8 gr. of distilled water is added. The polymerization is started at 80° C. to yield a solid resin.

EXAMPLE 31

20 kg. of acrylic acid and 6 kg. of acrylamide are dissolved in 9.5 kg. of distilled water and the acrylic acid is partially neutralized with 12 kg. of KOH. 0.036 kg. of methylenebisacrylamide as a polyvinyl monomer was added as well as 19.9 kg. of titanium dioxide to provide an aqueous mixed monomer mixture The mixed monomer mixture is mixed with 0.28 kg. of 2,2'-azobisisobutyronitrile, dissolved in 2 kg. of acetone as a polymerization initiator. This stirred mixture, at a temperature of 60° C., is transferred on an endless belt (600-700 mm. in width, and 7 m. in length) at a thickness of about 1 cm. The polymerization is initiated promptly on the belt resulting in a solid resin.

EXAMPLE 32

123.3 gr. of acrylamide is dissolved in 48.2 gr. of acrylic acid and 28.0 gr. of aqueous ammonia (29% concentration) is added for 70 mole percent neutralization of the acrylic acid. Next, 0.01 gr. of N,N'-methylenebisacrylamide and 1 gram of titanium dioxide are added and stirred to homogenize. As an initiator, 0.7 gr. of 2,2'-azobis(2-amidinopropane)dihydrochloride dissolved in 5 gr. of distilled water is added. The polymerization is initiated in a TEFLON coated glass reaction chamber kept at 80° C., yielding a solid porous resin having a water content of less than 15% by weight. The pulverized solid is surface treated with 0.6% of a polyquaternary amine.

EXAMPLE 33

15.8 gr. of acrylamide is dissolved in 44.2 gr. of acrylic acid. 28.0 gr. of aqueous ammonia (29% concentration) is added to neutralize 70 mole percent of the acrylic acid. Then 1 gram of titanium dioxide and 0.01 gr. of N,N'-methylenebisacrylamide are added. Next, as the initiator, 0.7 gr. of 2,2'-azobis(2-amidinopropane)-dihydrochloride dissolved in 5 gr. of distilled water is added. The solution is kept at 80° C. and polymerization is initiated with increased temperature resulting in a solid, porous resin.

It will be understood that the present disclosure has been made only by way of preferred embodiment and that numerous changes in details of construction, combination, and arrangement of parts can be resorted to without departing from the spirit and scope of the invention as hereunder claimed.

What is claimed and sought to be secured by Letters Patent of the United States is:

1. A process for preparing a solid water absorbing resin comprising mixing a solution of (A) acrylic acid neutralized 70–100 mole percent; (B) a non-reactive and water-insoluble metal oxide in an amount of about 0.001% to about 5% based on the total weight of the solution; and (C) a water-miscible to water-soluble polyvinyl monomer in a combined concentration of (A), (B) and (C) of at least 30 wt. %; with water to form a mixed solution wherein the monomers of the mixed solution consist essentially of (A) and (C) and initiating polymerization of monomers (A) and (C) such that during polymerization, the exothermic heat of reaction is substantially the only heat energy used to accomplish polymerization, crosslinking and to drive off sufficient water to obtain a solid crosslinked resin including metal oxide (B) and having a water content of 15 percent by weight or less.

2. A process as defined in claim 1 wherein the metal oxide (B) is essentially homogeneously distributed throughout the solid crosslinked resin.

3. A process as defined in claim 1 wherein the combined concentration of the monomers (A) and (C) and metal oxide (B) is at least 30 wt. % and less than 80 wt. %.

4. A process as defined in claim 1 wherein the metal oxide (B) is present in an amount of about 0.75% to about 3% based on the weight of acrylic acid.

5. A process as defined in claim 1 wherein the mixed solution has a temperature of 20 to 85° C. prior to polymerization.

6. A process as defined in claim 1 wherein monomer (C) is selected from the group consisting of N,N-methylenebisacrylamide and N,N-methylenebismethacrylamide.

7. A process as defined in claim 1 wherein the mixed solution contains 1 to 10 wt. % of an organic solvent based on the weight of (A), (B) and (C).

8. A process as defined in claim 1 wherein the mixed solution further contains an organic solvent having a boiling point of 40 to 150° C.

9. A process as defined in claim 1 wherein the metal oxide is selected from a group consisting of titanium dioxide, magnesium oxide, zinc oxide, barium oxide, zirconium oxide, calcium oxide, silicon dioxide, aluminum oxide, selenium dioxide, tin oxide, bismuth oxychloride, antimony trioxide, antimony pentioxide, beryllium oxide, cadmium oxide, cerium oxide, iron oxide, lead oxide, bismuth oxide, vanadium oxide, cobalt oxide, magnesium aluminum oxide, zinc aluminum oxide, magnesium titantium oxide, iron titanium oxide, calcium titanium oxide, and beryllium aluminum oxide; or mixtures thereof.

10. A process as defined in claim 1 wherein the metal oxide is selected from a group consisting of titanium dioxide, magnesium oxide, zinc oxide, barium oxide, calcium oxide, silicon dioxide, aluminum oxide, tin oxide, bismuth oxychloride, antimony trioxide, iron oxide, lead oxide, bismuth oxide, vanadium oxide, cobalt oxide, magnesium aluminum oxide, zinc aluminum oxide, magnesium titantium oxide, iron titanium oxide, and calcium titanium oxide; or mixtures thereof.

11. A process as defined in claim 1 wherein the metal oxide has a particle size ranging from about 10 microns to about 200 microns.

12. A process as defined in claim 1 wherein the metal oxide has a particle size ranging from about 50 microns to about 125 microns.

13. A process as defined in claim 1 further comprising surface treating the solid crosslinked resin with a sufficient amount of a polyquaternary amine to substantially increase the water absorption of the solid crosslinked resin.

14. A process as defined in claim 13 wherein the resin is treated with from about 0.1% to about 5.0% by dry weight of a polyquaternary amine.

15. A process as defined in claim 13 wherein the resin is treated with from about 0.25% to about 2% by dry weight of a polyquaternary amine.

16. A process as defined in claim 13 wherein the polyquaternary amine has a molecular weight from about 200 to about 5000.

17. A process as defined in claim 13 wherein the polyquaternary amine has a molecular weight from about 300 to about 4000.

18. A process for preparing a solid, water absorbing, crosslinked resin comprising:

combining a mixture of (A) potassium and/or ammonium acrylate; (B) a non-reactive and water-insoluble metal oxide in an amount of 0.0001% to 5% by weight based on the total amount of the mixture; and (C) a polyvinyl monomer, with water in an amount of at least 30 combined weight percent of (A) plus (B) plus (C) based on the total weight of (A) plus (B) plus (C) plus water to form a mixture wherein the monomers of the the mixture consist essentially of (A) and (C);

adding a polymerization initiator to said mixture capable of initiating, and in an amount sufficient to initiate polymerization of said mixture;

copolymerizing said mixture while utilizing the exothermic heat of reaction as substantially the only non-ambient energy source to drive water away from said polyacrylate resin copolymer to form said crosslinked resin copolymer, including the metal oxide (B) and having a water content sufficiently low to be powdered without an intermediate drying step.

19. A process as defined in claim 18 wherein the metal oxide (B) is essentially homogenously distributed throughout the crosslinked resin copolymer.

20. The process of claim 18 further including the step of adjusting the temperature of the mixture to a temperature of 25 to 85° C. prior to adding said polymerization initiator to said monomer mixture.

21. The process of claim 18 wherein said polymerization initiator is added in an amount of at least 0.5% total by weight of (A) and (C).

22. The process of claim 18 wherein the water content of said crosslinked resin copolymer incorporating the metal oxide is not greater than about 10% by weight as recovered from the polymerized mixture, without an additional drying step.

23. The process of claim 18 further including combining a non-aqueous solvent having a boiling point of 40–150° C. with said (A), (B) and (C) to form a porous resin.

24. The process of claim 18 including the step of pulverizing said crosslinked resin including the metal oxide to form a powder.

25. The process of claim 18 wherein the combined concentration of the monomers (A) and (C) and metal oxide (B) is at least 30 wt. % and less than 80 wt. %.

26. The process of claim 18 wherein the metal oxide is selected from the group consisting of titanium dioxide, magnesium oxide, zinc oxide, barium oxide, zirconium oxide, calcium oxide, silicon dioxide, aluminum oxide, selenium dioxide, tin oxide, bismuth oxychloride, antimony trioxide, antimony pentoxide, beryllium oxide, cadmium oxide, cerium oxide, iron oxide, lead oxide, bismuth oxide, vanadium oxide, cobalt oxide, magnesium aluminum oxide, zinc aluminum oxide, magnesium titanium oxide, iron titanium oxide, calcium titanium oxide, and beryllium aluminum oxide; or mixtures thereof.

27. The process of claim 18 wherein the metal oxide is selected from the group consisting of titanium dioxide, magnesium oxide, zinc oxide, barium oxide, calcium oxide, silicon dioxide, aluminum oxide, tin oxide, bismuth oxychloride, antimony trioxide, iron oxide, lead oxide, bismuth oxide, vanadium oxide, cobalt oxide, magnesium aluminum oxide, zinc aluminum oxide, magnesium titanium oxide, iron titanium oxide, and calcium titanium oxide; or mixtures thereof.

28. The process of claim 18 wherein the metal oxide has a particle size of from about 10 microns to about 200 microns.

29. The process of claim 18 wherein the metal oxide has a particle size of from about 50 microns to about 125 microns.

30. The process of claim 18 further comprising contacting the crosslinked resin copolymer with a polyquaternary amine in an amount of from about 0.1% to about 5.0% based on the weight of the crosslinked resin copolymer.

31. The process of claim 18 including the step of pulverizing the crosslinked resin copolymer to form a powder prior to contacting said powder with a polyquaternary amine in an amount of about 0.1% to 5.0% based on the weight of said crosslinked resin copolymer.

32. The process of claim 18 wherein the crosslinked resin copolymer is treated with from about 0.25% to about 2.0% of a polyquaternary amine based on the weight of the crosslinked resin copolymer.

33. The process of claim 31 wherein the crosslinked resin copolymer is treated with from about 0.25% to about 2.0% of a polyquaternary amine based on the weight of said crosslinked resin copolymer.

34. The process of claim 18 wherein the polyquaternary amine has a molecular weight from about 200 to about 5000.

35. The process of claim 18 wherein the polyquaternary amine has a molecular weight from about 500 to about 3000.

36. The process of claim 18 wherein the polyquaternary amine is a condensation product of hexamethylenediamine, dimethylamine and epichlorohydrin; a condensation product of dimethylamine and epichlorohydrin; or quaternized polyethylenimine.

37. The process of claim 18 wherein the polyquaternary amine is dispersed in methanol from about 0.1% to about 20% by weight before contacting the crosslinked resin copolymer.

38. A method of manufacturing a resin composition comprising mixing a solution of (A) acrylic acid, neutralized 70 to 100 mole percent, (B) a nonreactive and water-insoluble metal oxide in an amount of 0.001% to 5% based on the total weight of the solution; and (C) acrylamide in a mole ratio of (A):(C) in the range of 70:30 to 100:0; (D) a water soluble or water miscible polyvinyl monomer crosslinking agent in an amount of 0.001 to 0.6 percent by weight of (A) plus (B) plus (C); and water to form a mixed solution, wherein the monomers of the mixed solution consist essentially of (A), (C) and (D); and initiating polymerization of monomers (A), (C) and (D) such that during polymerization, the exothermic heat of reaction is substantially the only heat energy used to accomplish polymerization, crosslinking and to drive off sufficient water to form a water absorbing crosslinked polyacrylate resin composition including the metal oxide resin (B) and having a water content of 15 percent by weight or less.

39. The method of claim 38 wherein the metal oxide is essentially homogenously distributed throughout the water absorbing crosslinked polyacrylate resin composition.

40. The method of claim 38 wherein the metal oxide (B) is present in an amount of about 0.75% to about 3% based on the weight of acrylic acid.

41. The method of claim 38 wherein the water content of said crosslinked polyacrylate resin composition including the metal oxide is not greater than about 10% by weight as recovered from the mixed solution after polymerization, without an additional drying step.

42. The method of claim 38 including depositing said solution including the monomer mixture, the metal oxide and said initiator onto a support surface in sheet form for polymerization and crosslinking, followed by pulverizing the resultant crosslinked resin to form a powder, and thereafter contacting said powder with a polyquaternary amine in an amount of from about 0.1% to 5.0% based on the weight of said powder.

43. A method of absorbing aqueous liquids comprising mixing a solution of (A) acrylic acid, neutralized 70 to 100 mole percent; (B) a non-reactive and water-insoluble metal oxide in an amount of 0.001% to 5% based on the total weight of the solution; and (C) acrylamide in a mole ratio of acrylic acid:acrylamide in the range of 70:30 to 100:0; (D) a water soluble or water miscible polyvinyl monomer crosslinking agent in an amount of 0.001 to 0.6 percent by weight of (A) plus (B) plus (C); and water to form a mixed solution, wherein the monomers of the mixed solution consist essentially of (A), (C) and (D) and the concentration of (A), (B), (C) and (D) is below 70 percent by weight of the monomer solution prior to polymerization initiation; and initiating polymerization of monomers (A), (C) and (D) such that during polymerization, the exothermic heat of reaction is substantially the only heat energy used to accomplish polymerization, crosslinking and to drive off sufficient water to form a water absorbing crosslinked polyacrylate resin including the metal oxide (B) and having a water content of 15 percent by weight or less, and thereafter contacting said resin with an aqueous liquid to absorb said aqueous liquid into said resin.

44. The method of claim 40 further comprising contacting the crosslinked polyacrylate resin with a polyquaternary amine in an amount of from about 0.1% to about 5.0% based on the weight of said resin after forming the polyacrylate resin, and thereafter contacting said polyquaternary amine treated resin with an aqueous liquid to absorb said aqueous liquid into said resin.

* * * * *